United States Patent [19]

Warren et al.

[11] Patent Number: 5,368,701

[45] Date of Patent: Nov. 29, 1994

[54] PROCESS FOR FORMING ZINTL PHASES AND THE PRODUCTS THEREOF

[75] Inventors: Christopher J. Warren, Alden, Pa.; Robert C. Haushalter, Little York; Andrew B. Bocarsly, Princeton, both of N.J.

[73] Assignees: NEC Research Institute, Inc.; Princeton University, both of Princeton, N.J.

[21] Appl. No.: 75,026

[22] Filed: Jun. 11, 1993

[51] Int. Cl.$^5$ .............................................. C25B 3/12
[52] U.S. Cl. ............................................. 204/59 QM
[58] Field of Search ................................. 204/59 QM

[56] References Cited

U.S. PATENT DOCUMENTS 4,617,204 10/1986 Haushalter ............................. 427/304
4,626,296 12/1986 Haushalter et al. ................... 148/403

OTHER PUBLICATIONS

M. M. J. Treacy et al, "Transmission Electron Microscopy Study of the Reaction of $Sn^4_9$-Zintl ions with Single Crystal Au Films", Ultramiscroscopy 23 pp. 135-150. May 20, 1987.

J. W. Foise et al, "Unusual Magnetic Behavior of the Amorphous Metallic Materials, $M_2SnTe_4$ Where M=Co And Ni", Solid State Communications, vol. 63, No. 4, pp. 349-351, 1987. Date not available.

Robert C. Haushalter et al, "Synthesis of New Amorphous Metallic Spin Glasses $M_2SnTe_4$ (M=Cr, Mn, Fe, Co): Solvent Induced Metal-Insulator Transformations**", Angewandte Chemie, vol. 23, No. 2 Feb. 1984, pp. 169-170.

L. Diehl et al, "Zintl's Inorganic Polyhedron Compounds, III Polyanonic Salts": Preparation and Properites of the Cyrstalline Compounds [$Na_4$ 7en]$Sn_9$, [$Na_4$ 5en] [$Ge_9$, and [$Na_3$ 4en]$Sb_7$ and of their Solutions The Crystal Structure of [$Na_4$ 7en]$Sn_9$, Chem. Ber. 109, pp. 3404-3418 (1976) (month not available).

R. Haushalter et al, "Novel Method for the Electroless Metallization of Polymide: Surface Oxidation of Zintl Anions", Polyimides, vol. 2, 1984, pp. 735-750 (month not available).

R. C. Haushalter et al, "Chemical Control of the Electronic Properties in the Amorphous Alloys $M_2SnTe_4$(M=Mn, Fe, Co, Cu)", Mat. Res. Bull. vol. 22, pp. 761-768, 1987. (month not available).

Dieter Kummer et al, "Preparation and Properties of a Crystalline Compound $Na_4Sn_9$. 6-Ethylenediamine(**)", Angew Chem, Internat. Edit. (vol. 9 (1970) No. 11 pp. 895.

B. Stnaley Pons et al, "Electrochemical Generation of the Naked Metal Anionic Clusters, $Sn_{9-x}Pb^{4-}x$ (x=0 to 9)". Electrochimica Acta., vol. 26 pp. 365-366, May 30, 1980.

Edwin Garcia et al., "Quaternary Ammonium Amalgams as Zintl Ion Salts and Their Use in the Synthesis of Novel Quaternary Ammonium Salts", J. Am. Chem. Soc. 1986, 108, pp. 6082-6083. Exact date not available.

Ralph E. Rudolph et al, "Naked-Metal Clusters in Solution. 4. Indicaitons of the Variety of Cluster Species Obtainable by Extraction of Zintl Phases: $Sn_4^{2-}$, $TISn_8^{5-}$, $SN_{9-x}Ge_x^{4-}(x=0-9)$, and $SnTe_4^{4-}$", J. Am. Chem. Sco. 1981, 103, pp. 2480-2481. Exact date not available.

L. Diehl et al, "Inorganic Polyhedral Compounds, II Zintl's Polyanionic Salts: Synthesis of the Crystalline Compounds [$Na_4$.7 en[$Na_4$.5 en ]$Ge_9$ and [$Na_3$.4 en]$Sb_7$. The Crystal Structure of [Na.7en[$Sn_9$", Z. Naturforsch, 31b, 522-524, 1976; eingegangen am 16. Feb. 1976 English Abstract Only.

*Primary Examiner*—John Niebling
*Assistant Examiner*—Brendan Mee
*Attorney, Agent, or Firm*—Arthur J. Torsiglieri

[57] ABSTRACT

Crystalline solids including Zintl anions have been synthesized by an electrolytic process that uses a cathode whose composition is an alloy including the elements forming the Zintl ion and an electrolyte that comprises a solvent that is basic and polar, such as ethylenediamine, and a supporting electrolyte, advantageously organic, that provides a suitable cation for the Zintl anion. Specific examples of solids that have been crystallized include tetraphenylphosphonium gold telluride, tetraphenylphosphonium gallium telluride, and tetrapropylammonium antimony telluride.

12 Claims, 4 Drawing Sheets $[Au_3Te_4]^{3-}$ $[Au_2Te_4]^{2-}$

○ Au   ⊘ Te $[GaTe_2(en)_2]^{1-}$

○ Ga  ◐ Te  ⊕ C  ◓ N

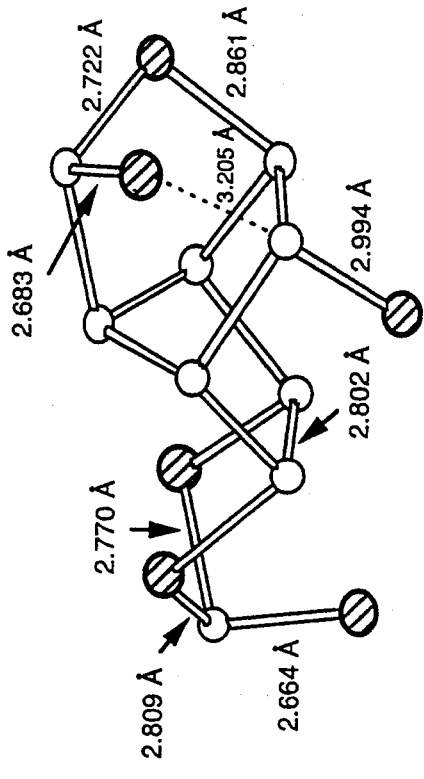
Fig 4B [Sb₉Te₆]³⁻
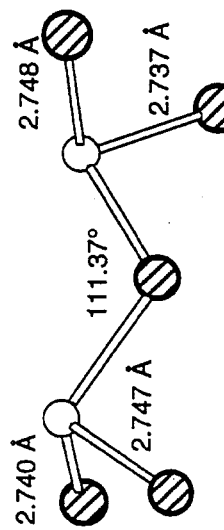
Fig 4C [Sb₂Te₅]⁴⁻
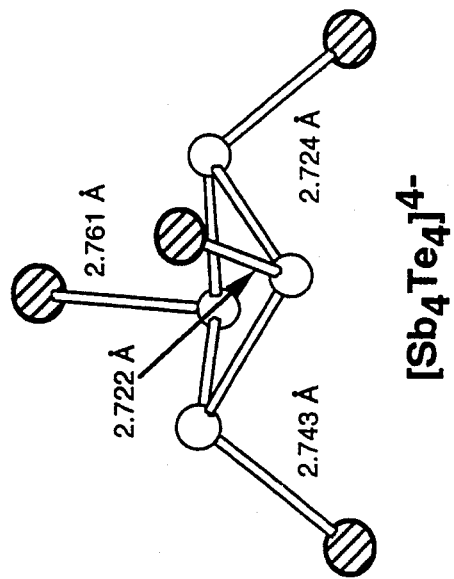
Fig 4A [Sb₄Te₄]⁴⁻
○ Sb  ⊘ Te Fig 5A
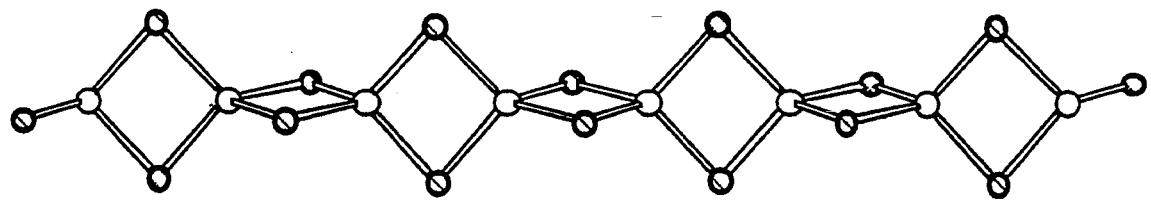
Fig 5B
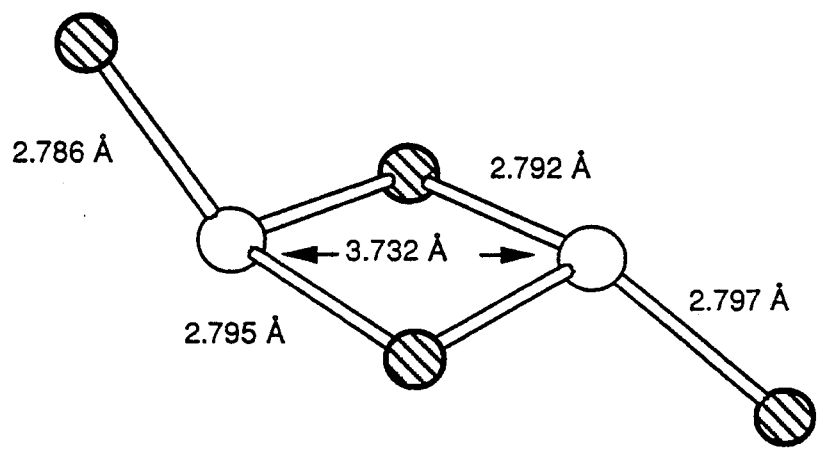
$[In_2Te_4]^{2-}$

PROCESS FOR FORMING ZINTL PHASES AND THE PRODUCTS THEREOF

FIELD OF INVENTION

This invention relates to electrolytic processes for forming crystalline Zintl phases and to novel compositions produced by such processes.

BACKGROUND OF THE INVENTION

In the early 1930's, Zintl and coworkers showed that the electrolysis of certain main group, main group alloy, and intermatallic phases could produce metal polyanions in the catholyte. Through the potentiometric titrations of liquid ammonia solutions of these salt-like intermetallic compounds, and exhaustive extractions of alkali metal alloys of the heavier group 14 and 15 elements, they were able to deduce the existence of $Sn_9^{4-}$, $Pb_9^{4-}$, $Pb_7^{4-}$, $As_3^{3-}-As_7^{3-}$, $Sb_7^{3-}$, $Sb_3^{3-}$, $Bi_7^{3-}$, $Bi_5^{3-}$ and $Bi_3^{3-}$ but apparently did not isolate crystalline derivatives of these species to confirm their findings. These metal polyanions, which have come to be known as Zintl phases, are unique in that they have no exopolyhedral ligands at the vertices and so can easily form metal—metal bonds, which make them ideal precursors for the preparation of conducting and semiconducting films and solids by topochemical or bulk oxidations, respectively. Such films might have a variety of uses, including use as coatings. The novel polyanions of the present invention should have the same uses.

Additionally, after an initial report in 1970 on the ethylenediamine extraction and isolation of $Sn_9^{4-}$ from $Na_4$, $Sn_9$, a variety of homopolyatomic and heteropolyatomic anions have been isolated via the solvent extraction of Zintl phases including $Se_6^{2-}$, $Te_4^{2-}$, $Tl_2Te_2^{2-}$, $TlSn_8^{-3}$, $As_2Se_6^{3-}$, $SnTe_4^{4-}$, $Sn_2Te_6^{4-}$, $HgTe_{12}^{4-}$, $As_{10}Te_3^{2-}$ among others. These are seen to include Group 16 elements in addition to Group 14 and 15 elements.

The term Zintl phase has often been used to define an intermetallic compound comprising one element of the alkali and/or alkaline earth metals and one or more elements from the main group elements. It will be used herein to define a compound that has been prepared electrolytically and that comprises an organic cation and a polyanion involving a metal-to-metal bond of atoms of the same or different metals of the main group or transition group of metals. Moreover, as used herein gallium, germanium, aresenic, selenium, indium, tin, antimony, tellurium, thallium lead and polonium are considered to be the main group of metals while titanium, vanadium, chromium, manganese, iron, cobalt, nickel, copper, zirconium, niobium, molybdenum, technetium, ruthenium, rhodium, palladium, silver, hafnium, tantalum, tungsten, rhenium, osmium, iridium, platinum and gold are considered to be the transiton group metals. Such a polyanion will also be referred to as a Zintl anion.

SUMMARY OF THE INVENTION

The present invention relates to a process that involves the novel synthesis of structurally characterized crystalline solids by the cathodic dissolution of alloy electrodes including the main elements of the solid, advantageously by the use of a catholyte that includes an organic salt. In particular by the use of gold tellurium alloy cathodes we have been able to synthesize crystals of $(TBA)_3Au_3Te_4$ where $(TBA)^+$ is tetra-n-butylammonium $[(n-C_4H_9)_4N]^+$, and that compound is to be designated hereinafter as compound (1) and $(TPP)_2Au_2Te_4$, where $(TPP)^+$ is tetraphenylphosphonium $[(C_6H_5)_4P]^+$, and that compound is to be designated hereinafter as compound (2). Compounds of gold and tellurium have become of particular interest as possible erasable laser recording media and as indicators of the geochemical formation conditions of minerals. We have also isolated the compounds, $(TPP)GaTe_2(en)_2$, where (en) is ethylenediamine, to be designated compound (3); $(TPA)_4Sb_4Te_4$, where $TPA^+$ is tetraproppylammonium $[(n-C_3H_7)N]$, to be designated compound (4), $(TPA)_3Sb_9Te_6$, to be designated compound (5), $(TMA_4)$ $Sb_2Te_5$, where (TMA) is tetramethylammonium, $[(CH_3)_4N]^+$ to be designated compound (6), and $(TBA)_2In_2Te_4$, to be designated compound (7).

The invention will be better understood from the following more detailed description taken in conjunction with the accompanying drawing.

BRIEF DESCRIPTION OF THE DRAWING

FIGS. 4A, 4B and 4C show the structure of the polyanion of compound (4), (5) and (6), respectively.

FIG. 5A shows the structure of the chain of polyanions of compound (7) and FIG. 5B of a link of the chain.

DETAILED DESCRIPTION OF THE INVENTION

Figure 1:
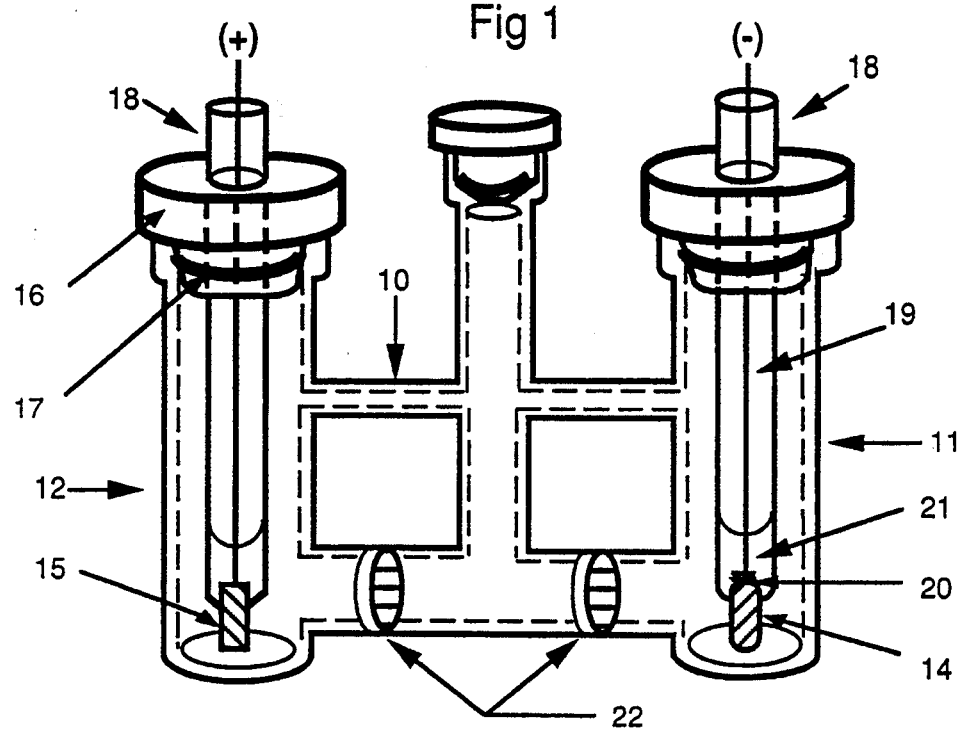
FIG. 1 shows the electrochemical cell used in the process of the invention.

FIG. 1 shows an electrochemical cell that comprises basically a glass envelope 10 with two main compartments 11 and 12. Cathode compartment 11 houses the cathode electrode 14. Anode compartment 12 houses the anode counterelectrode 15. Each open end of the two chambers is sealed with a Teflon bushing 16 and a silicone O-ring 17. Electrical contact from the external current terminals 18 to each of the two electrodes is provided by a copper wire 19. The copper wires are soldered to their respective electrodes, typically by an indium-tin solder 20, and each connection region is shielded from the electrolyte by epoxy 21, leaving only the electrodes exposed to the electrolyte. Fine porosity frits 22 each of 20 millimeter diameter are included between the two compartments to limit any solid flow between the two compartments 11, 12. An external power source (not shown) is connected between the two external terminals to flow current between the electrodes in the usual fashion.

The cathode electrode typically is an alloy containing the elements of the Zintl phase to be synthesized. In the case of $AuTe_2$ phase, an $AuTe_2$ alloy is made by melting stoichiometric amounts of the two elements under a nitrogen atmosphere in a quartz tube and the resulting regulus is then crushed into a fine power and recast into a cylindrical shape onto which a copper wire is attached with 50/50 indium tin solder.

The anode electrode is chosen of a metal that will be little affected by the electrolyte. Both platinum and nickel electrodes have been used successfully for this purpose, although the nickel has proved preferable in some instances, as it generates an insoluble precipitate in the anode chamber, thus minimizing cross contamination of the cathodic chamber with oxidation products from the anode chamber.

The solvent should be basic and polar for the crystallization to proceed. Ethylenediamine has proved particularly suitable as the solvent. However, other basic polar liquids known to be useful as solvents should function adequately. The supporting electrolyte should be one that can provide a cation that is suitable for crystallization with the Zintl polyanion; organic electrolytes particularly quarternary ammonium and phosphonium cations have proven advantageous, presumably because of their large cation. The choice of the supporting electrolyte has been found to affect the form of polyanion formed, as will appear in the later discussion.

The cathodic dissolution of a $AuTe_2$ alloy electrode (surface area of 1 square centimeter) in 20 ml of a 0.4M solution of TBA-I in en (which was distilled from a red solution of $K_4Sn_9$ under an inert atmosphere) that ran at a constant current of $300\mu A$ immediately gave rise to a deep purple/brown stream of polyanions, and after 2 days yielded dark brown rectangular crystals of compound (1) in greater than 60% yield based on the gold dissolved (electrochemical yield=26%). Crystals of compound (1) were found growing on the $AuTe_2$ cathode and throughout the walls of the cathode chamber. Accordingly, a thin layer of the crystalline solid can be deposited on an insulating substrate, such as a glass slide, by locating such substrate, in the cathode chamber. Upon removal of the substrate, the layer should be coated before exposure to an oxidizing atmosphere. Varying the current from $100\mu A$ to 1mA in the above experiment had no effect on the product, yielding compound (1) in all cases. A control experiment of powdered $AuTe_2$ and tetrabutylammonium iodide (TBA-I) in ethylenediamine (en) did not give rise to any color (no polyanions).

Figure 2A:
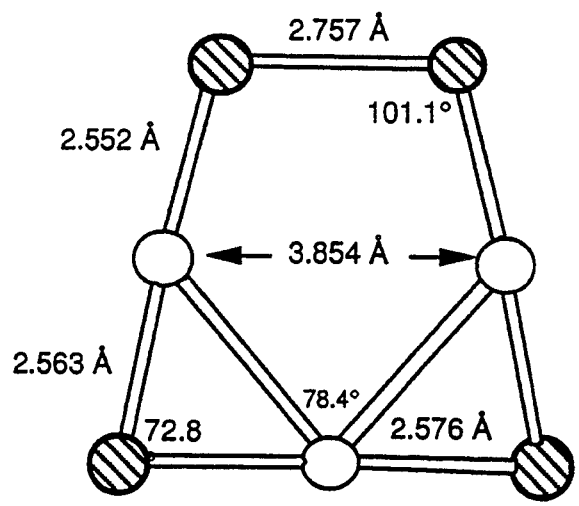
FIG. 2A shows the structure of one of the two crystallographically independent $[Au_3Te_4]^{3-}$ anions in compound (1)

X-ray structural analysis of compound (1) at 235 K revealed the novel $[Au_3Te_4]^{3-}$ anion that is shown in FIG. 2A. There are two slightly puckered, crystallographically independent $[Au_3Te_4]^{3-}$ anions in the unit cell, each possessing crystallographic 2-fold symmetry in the solid state. The central Au atom in a given $[Au_3Te_4]^{3-}$ anion resides on the Wyckoff 4e special position in space group C2/c, lying on a c-glide plane. Each $[Au_3Te_4]^{3-}$ anion contains three Au(I) atoms joined together by Au—Au bonds of 3.049(3)Å or 3.015(3)Å and making Au-Au-Au angles of 78.4(1)° or 81.1(1)° respectively. These Au—Au distances are somewhat longer than the 2.8Å Au—Au distances observed in gold metal. The transannular non-bonded Au—Au distance is either 3.922(4)Å or 3.922(4)°. As expected for Au(I), the Te-Au-Te angles are all close to 180°, varying from 172.5(2)° to 178.9(1)°. Au-Te bonds range from 2.549(4)Å to 2.589(3)Å, and the Te—Te distances of 2.757(8)Å and 2.760(7)Å are similar to the Te—Te contacts observed in other structurally characterized tellurides.

Figure 2B:
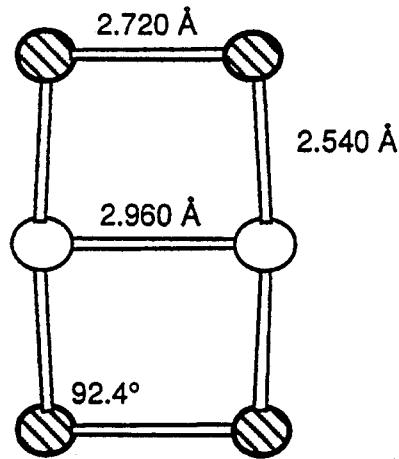
FIG. 2B shows the structure of the $[Au_2Te_4]^{2-}$ anion in compound (2)

Changing the cation has a profound effect on the course of the reaction. If, for instance, the supporting electrolyte is changed to tetraphenylphosphonium bromide (TPP.Br), an intense deep red color streams from the cathode, and after 3 days in 20 ml of a 0.5M TPP.Br in en at a current density of ca. 300 $\mu A.cm^{-2}$, one isolates dark red needles of compound (2) in approximately 40% yield (electrochemical yield=10%). X-ray structural analysis of compound (2) revealed the $[Ae_2Te_4]^{2-}$ anion which had been previously synthesized by the $[(Ph_3P)_2N]$.Cl/en extraction of K $AuTe_2$, $K_2AuAsTe_3$ and $K_3AuGeTe_3$, as reported by R. C. Haushalter "Inorg Chem Acta" (1985), 102 L 37. The $[Au_2Te_4]^{2-}$ anion is shown in FIG. 2B. This anion is planar (to within 0.026 Å) and lies on a crystallographic inversion center. It has essentially the same Te—Te distances and Te-Au-Te angles as those observed in $[Au_3Te_4]^{3-}$.

The invention has also been used to synthesize a new gallium telluride anion included in $(TPP)GaTe_2(en)_2$, designated as compound (3).

The synthesis of compound (3) used a $Ga_2Te_3$ electrode which is made by melting stoichiometric amounts of the elements under $N_2$ in a quartz tube. When melting, these elements react violently erupting in bright orange flames and leaving a shiny black solid as a product. The regulus is then crushed into a fine powder and fabricated into electrodes in accord with the procedure reported for the Au-Te system. Compound (3) was observed as bright orange needle-shaped crystals which grew from a galvanostated $Ga_2Te_3$ cathode running at a current density of about 300 $\mu Acm^{-2}$ for 6 days in a solution of 0.5M tetraphenylphosphonium bromide in ethylenediamine (which as mentioned above, was prepared by distillation from a red solution of $K_4Sn_9$ under an inert atmosphere). The two compartment, liquid junction, air-tight electrochemical cell of FIG. 1, equipped with a nickel plate counter electrode, was utilized for this purpose. The use of nickel as a counter electrode is a modification to the technique used for gold tellurides (in which Pt was used), and it is advantageous in that it generates an insoluble purple precipitate (the qualitative microprobe analysis of which showed Ni and Br in a 1:2 molar ratio) in the anodic compartment. This helps reduce cross-contamination of the cathode compartment with oxidation products from the anode compartment thus allowing the reactions to run for longer periods of time.

Figure 3A:
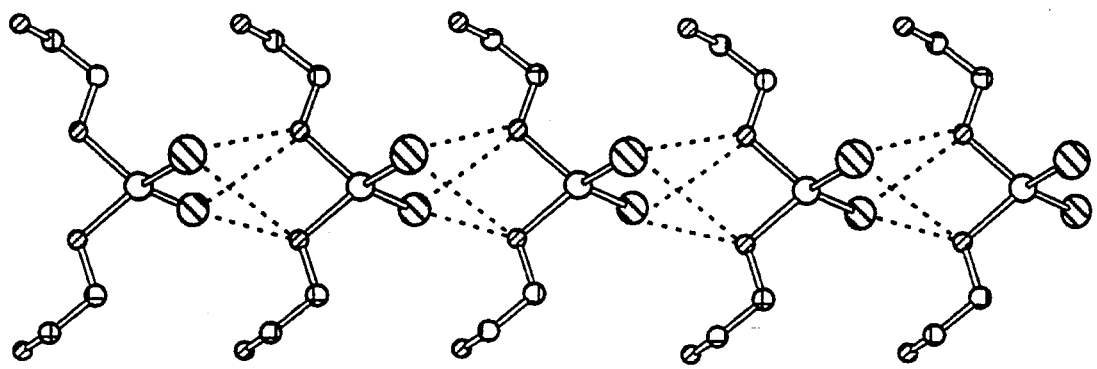
FIG. 3A shows the structure of a one-dimensional chain of polyanions of compound (3) and FIG. 3B of a link of the chain.
Figure 3B:
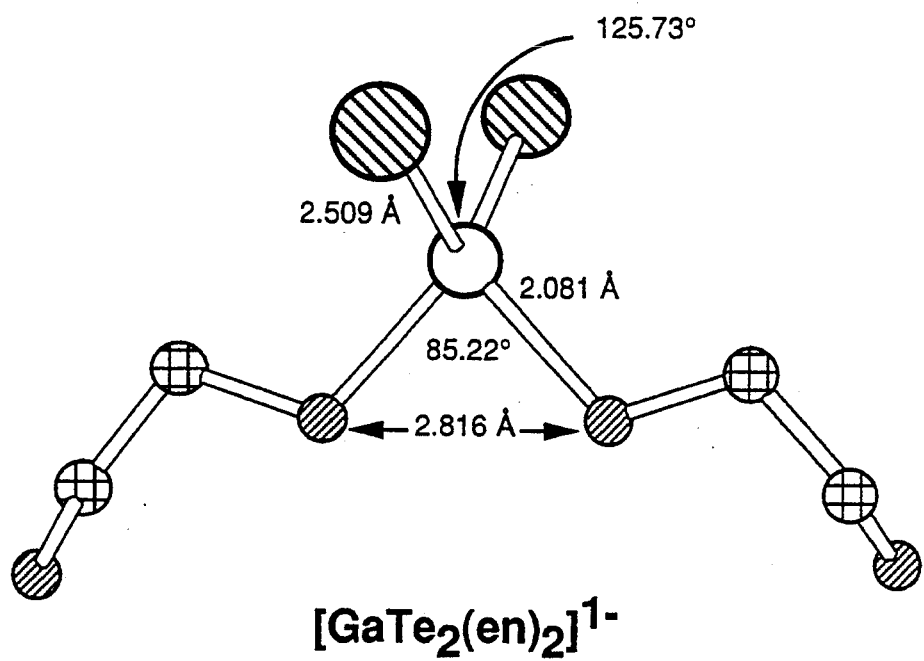

X-ray structural analysis of compound (3) revealed the novel $GaTe_2(en)_2{}^{1-}$ anion which is shown in FIG. 3A. The anion consists of Ga(III) in a distorted tetrahedral coordination environment. The Ga atom lies on the Wycoff 4e special position in space group C2/c on a 2-fold axis and is bonded to two crystallographically equivalent terminal Te atoms. The Ga-Te bond distance is 2.509(1)Å, which is 0.111 Å shorter than the sum of the Ga and Te covalent radii, 2.62 Å. Due to the paucity of structurally characterized Ga-Te compounds, it is difficult to make extensive comparisons with this Ga-Te bond distance. The four-membered $Ga_2Te_2$ ring in $[(Me_3CCH_2)_2GaTePh]_2$ has Ga-Te bond distances in the range 2.7435(8)–2.7623(8)Å, and $K_6Ga_2Te_6$ is composed of two edge-sharing $GaTe_4$ tetrahedra with Ga-Te bond distances of 2.591Å $(terminal)$ and 2.680Å$(bridging)$. In the solid state phases, the average Ga-Te bond distances in GaTe (monoclinic), GaTe (hexagonal), $Ga_2Te_3$ and $Ga_2Te_5$ are 2.665, 2.61, 2.56, and 2.641Å respectively. Therefore, it would appear that the $GaTe_2(en)_2{}^{1-}$ anion has the shortest Ga-Te bond distance thus far recorded.

The Te-Ga-Te bond angle of 125.7(1)° is greatly distorted from the ideal tetrahedral angle of 109.5° by the repulsion of the large Te atoms which are 4.465Å apart. The N-Ga-N angle is 85.2(4)°, bringing the inner ethylenediamine N atoms to within 2.816Å of each other. The Te-Ga-N angles are 110.0(2)° and 109.2(2)°.

The complete structure of compound (3) consists of GaTe$_2$(en)$_2^-$ anions which are doubly hydrogen bonded into one-dimensional chains with N-Te contacts of 3.750(7)Å and 3.793(7)Å, as shown in FIG. 3A. Unlike the corresponding sulfides and selenides, there are few examples of hydrogen bonding to telluride anions. Hydrogen bonding of an ethylenediamine molecule to Te$_3^{2-}$ has been observed with an N-Te distance of 3.46(6)Å, and CH$_3$OH has also observed to hydrogen bond to the ends of a Te$_4^{2-}$ anion with the O-Te distance being 3.585(7)Å. In compound (3) however, we are dealing with two hydrogen bonds per tellurium atom and a formal Te$^{2-}$ anionic radius instead of a Te atomic radius, both reasons of which may contribute to the longer observed hydrogen bonding distances.

The individual chains of GaTe$_2$(en)$_2^{1-}$ run parallel to the crystallographic b axis in sheets which are effectively isolated from one another by tetraphenylphosphonium cations. Individual chains within these rows have terminal ethylenediamine N—N contacts of 3.46(1)Å, and are clearly not related by hydrogen bonding interactions. The Te—Te distance between rows of GaTe$_2$(en)$_2^{1-}$ chains is 9.789Å.

The mechanism of formation of GaTe$_2$(en)$_2^{1-}$ from the reaction of a Ga$_2$Te$_3$ cathode is thought to involve the dissolution of a GaTe$_2$ fragment to which ethylenediamine molecules can then coordinate (in a monodentate fashion, as they are in excess), thus forming a stable tetrahedral Ga (III) moiety. There is no evidence of excess polytellurides in the catholyte solution (light orange in color), and evaporation of the ethylenediamine results in the formation of an orange powder, the qualitative microprobe analysis of which shows Ga and Te in a 1:2 molar ratio. By simply exposing this orange solution to the air, we obtained a black powder which contains Ga and Te.

Additionally, this technique has been used to synthesize three new antimony tellurides (TPA)$_4$Sb$_4$Te$_4$, designated as compound (4), and (TPA)$_3$Sb$_9$Te$_6$, designated as compound (5), and (TMA)$_4$Sb$_2$Te$_5$ designated as compound (6), all of which exist as discrete anions in the solid state and are synthesized from the cathodic dissolution of a Sb$_2$Te$_3$ alloy electrode in the manner previously described.

There are very few examples of antimony telluride compounds in the literature. Apart from the known binary phase Sb$_2$Te$_3$, there appears to be only four other known polyanion structures: BaSbTe$_3$, LiSbTe$_2$, K$_3$SbTe$_3$ and AgSbTe$_2$. There also exist several mixed antimony germanium telluride compounds such as GeSb$_4$Te$_7$, GeSb$_2$Te$_4$ and Ge$_2$Sb$_2$Te$_5$ which have been studied for their potential semiconducting properties. All of these earlier compounds have been prepared by the high temperature fusion of the elements.

Compounds (4) and (5) were prepared by the cathodic dissolution of a Sb$_2$Te$_3$ electrode that was made by first melting stoichiometric amounts of the elements under nitrogen in a quartz tube. The resulting silver solid was then crushed into a fine powder and fabricated into electrodes in accord with the procedure reported above for the Au-Te system. The synthesis was again done in the same two-compartment, liquid junction, air-tight electrochemical cell, equipped with a nickel plate counter electrode. The cell was filled with a 0.56M solution of tetrapropylammonium bromide (TPA.Br) in ethylenediamine. All manipulations were performed in a high purity (<1 ppm O$_2$) He atmosphere.

The cathodic dissolution of a Sb$_2$Te$_3$ alloy electrode running at a current density of about 300 $\mu$Acm$^{-2}$ immediately gave rise to a deep brown stream of anion which surrounded the cathode and then slowly sank to the bottom of the cathode chamber. After one day, a red-brown crystalline solid, which was later identified as (TPA)$_4$Sb$_4$Te$_4$, was observed growing on the Sb$_2$Te$_3$ cathode. After approximately 2 days, the deep brown catholyte solution also yielded brown spear-shaped crystals of (TPA)$_3$Sb$_9$Te$_6$ which were found growing on the bottom of the chamber. It is unknown if Sb$_9$Te$_6^{3-}$ forms directly from the cathodic dissolution process, or if Sb$_4$Te$_4^{4-}$ is somehow converted to Sb$_9$Te$_6^{3-}$ on standing in the electrolyte solution. The reaction was isolated after 5 days yielding compounds (4) and (5) in an approximate 80:20 ratio. These two anions appear to be products only of the electrochemical dissolution reaction, and are not obtained from a control experiment of powdered Sb$_2$Te$_3$ and TPA.Br in en.

The compound (4) crystallizes in space group Pbcn with 8 Sb$_4$Te$_4^{4-}$ anions in the unit cell. The structure of the Sb$_4$Te$_4^{4-}$ anion is shown in FIG. 4A. The anion consists of a folded Sb$_4$ ring, to which four terminal Te atoms are attached in the equatorial positions, and displays approximate, but not crystallographically imposed, 2 mm point group symmetry in the solid state. This geometry is quite different from the bare Sb$_2^{2-}$ anion which exists as a square planar moiety, but more closely resembles that of the compound (t-Bu)$_4$Sb$_4$ which has t-Bu groups bonded to a folded Sb$_4$ ring in equatorial positions. The Sb—Sb distances in compound (4) are in the range 2.836(4)–2.883(4)Å, and can be compared to those in the t-Bu compound which fall in the range 2.814(2)–2.821(2)Å. The average transannular non-bonded Sb—Sb distance in 4 is 3.913 Å. For comparison, the average Sb—Sb distance in the Sb$_4^{2-}$ anion is 2.750 Å, and it has an average transannular non-bonded Sb—Sb distance of 3.889 Å. The Sb-Te bond distances in Sb$_4$Te$_4^{4-}$ are in the range 2.722(4)–2.761(4)Å. Due to the paucity of structurally characterized Sb-Te compounds, it is difficult to make extensive comparisons with these Sb-Te bond distances. The ternary Zintl phase compound, K$_3$SbTe$_3$, consists of discrete trigonal pyramidal anionic units having three equivalent terminal Sb-Te bond distances of 2.7831(7)Å. The Sb-Te bond distance in the solid state phase Sb$_2$Te$_3$ is 2.974 Å, and Sb-Te distances in BaSbTe$_3$ are in the range 2.832–3.090 Å.

Compound (5) crystallizes in monoclinic space group P2$_1$/c with 4 Sb$_9$Te$_6^{3-}$ anions in the unit cell. The structure of the Sb$_9$Te$_6^{3-}$ anion is shown in FIG. 4B. The assignment of Sb and Te atoms in this anion was based on their chemically reasonable connectivities and an elemental microprobe analysis which yielded a Sb:Te ratio of 1.5:1. The Sb$_9$Te$_6^{3-}$ anion can be thought of as the fusion of two well known structure types: a bicyclic Sb$_7$Te$_4$ moiety with a Sb—Sb transannular closure closely resembling that of Se$_8^{2+}$ part of which is shared to form a Sb$_6$Te$_2$ cage that resembles the ones found in X$_4$N$_4$ (X=As, S, Se), X$_4$S$_4$ (X=P, Te) and As$_4$Se$_4$.

Sb—Sb distances in Sb$_9$Te$_6^{3-}$ are in the range 2.756(5)–2.871(5)Å and internal Sb-Te distances vary from 2.722(7)–2.878(5)Å, all of which are comparable to those in the Sb$_4$Te$_4^{4-}$ anion and in other structurally characterized antimony tellurides.

Compound (6), $(TMA)_4Sb_2Te_5$ was prepared by the cathodic dissolution of an $Sb_2Te_3$ alloy electrode running at current density of about 100 microamperes per $cm^2$ in a 0.25M tetramethylammonium iodide solution of ethylenediamine. This compound was observed as dark brown plates that grew on the cathode after about 5 days.

The anion consists of two $SbTe_3$ trigonal bipyramids sharing a corner with an Sb-Te-Sb angle of 111.37°. Sb-Te distances in the anion range from 2.737(5)Å to 2.854(4)Å and are comparable to those found in compounds (4) and (5).

Other crystals that have been produced by this process include compound (7), $(TBA)_2In_2Te_4$. This compound was prepared using an $In_2Te_5$ alloy for the cathode electrode made by melting stoichiometric amounts of the elements under $N_2$ in a quartz tube. The regulus was then crushed into a fine powder and formed into an electrode in the manner similar to that previously described.

The cathodic dissolution of the $In_2Te_5$ cathode electrode at a current density of about 1 milliampere per $cm^2$ in 0.4 molar TBA gave rise to a deep red stream of anions. After one day, transparent yellow plate-like crystals had been deposited on the cathode and throughout the cathode compartment. After three days the crystals were recovered from the dark red solution by filtering in a helium atmosphere. Based on the moles of indium consumed, the yield was approximately 30 per cent.

A single crystal x-ray analysis of the yellow plates revealed the compound $(TBA)_2In_2Te_4(7)$ which crystallizes in monoclinic space group $P2_{1/c}(\#14)$ with a=14.86(2), b=15.740(4), c=18.262(4)Å, V=4243(5)Å$^3$ and Z=4. As seen in FIG. 5A, the structure consists of one-dimensional $(In_2Te_4)^{2-}$ chains that run parallel to the crystallographic c axis. These anions are separated from one another by tetrabutylommonium cations.

The electrochemical cathodic dissolution technique described here, depends on the crystallization of the constantly increasing concentration of anions, as the cathode dissolves, with the relatively large cations provided by the organic electrolyte. This technique should be widely applicable to the synthesis of new and useful compounds not realizable by standard hydrothermal and other high temperature elemental fusion techniques commonly used for the synthesis of other compounds obtained from the reaction of alkali or alkaline earth metals with the heavier main group or transition group of metals that have become known as Zintl phases.

Accordingly, it is to be understood that the specific examples described are merely illustrative of the general principles of the invention and it is expected that various modifications thereof will be devised without departing from the spirit and scope of the invention. In particular, other polyamines with 2–4 carbon atoms, particularly 2-3 carbon atoms such as isoproplyenediamine and isobutylenediamine should be useful solvents in place of ethylenediamine.

What is claimed:

1. An electrolytic process for preparing a Zintl phase solid comprising the steps of providing in an electrolytic cell a cathode electrode of an alloy composition that includes a component that will provide during electrolysis a Zintl polyanion,
   providing in the electrolytic cell an anode electrode,
   providing in the electrolytic cell a catholyte that includes a cation that will combine with the Zintl polyanion provided by the cathode electrode composition during electrolysis,
   applying between the cathode and anode electrodes a current adequate for causing dissolution of the cathode electrode for a time sufficient to form in the electrolytic cell a Zintl phase solid that includes the polyanion provided by the electrolysis of the cathode alloy compound,
   and recovering the Zintl phase solid from the electrolytic cell for utilization.

2. The process of claim 1 further characterized in that the cathode electrode composition includes tellurium and is capable of providing a tellurium-rich polyanion whereby the Zintl phase solid formed and recovered is tellurium-rich.

3. The process of claim 2 which is further characterized in that the cathode electrode composition further includes an element chosen from the group consisting of gold, gallium, antimony and indium and such element is included in the tellurium-rich polyanion and in the Zintl phase solid formed and recovered.

4. The process of claim 1 in which the catholyte comprises an organic solvent chosen from the group consisting of ethylenediamine, isobutylenediamine and isopropylenediamine.

5. The process claim 4 in which the catholyte further includes as the supporting electrolyte a composition chosen from the group consisting of tetrabutylammonium, tetraphenylphosphonium, tetramethylammonium and tetrapropylammonium.

6. The process of claim 1 in which the cathode electrode is included in a cathode compartment and the anode electrode is included in an anode compartment and solid flow between the two compartments is limited.

7. The process of claim 1 in which the catholyte of the electrolytic cell comprises an organic solvent chosen from the group consisting of ethylenediamine, isopropylenediamine and isobutylenediamine and a supporting electrolyte chosen from the group consisting of salts of tetrabutylammonium, tetrphenylphosphonium, tetramethylammonium and tetrapropylammonium.

8. The process of claim 1 in which the cathode electrode alloy includes an element chosen from the group consisting of gold, gallium, antimony, indium and tellurium.

9. The process of claim 1 in which the cathode electrode alloy includes tellurium and an element chosen from the group consisting of gold, gallium, antimony and indium arsenic.

10. The process of claim 7 in which the cathode electrode alloy includes an element chosen from the group consisting of gold, gallium, antimony, indium and tellurium.

11. The process of claim 1 in which the cathode electrode is a gold tellurium alloy.

12. The process of claim 7 in which the cathode electrode is a gold tellurium alloy.

* * * * *